United States Patent [19]

Kurtz et al.

[11] 4,034,008
[45] July 5, 1977

[54] PROCESS FOR PREPARING UNSATURATED ACIDS AND ALDEHYDES

[75] Inventors: Abraham Nathan Kurtz; Erlind Magnus Thorsteinson; Harry Joe Decker, all of Charleston, W. Va.

[73] Assignee: Union Carbide Corporation, New York, N.Y.

[22] Filed: Aug. 25, 1975

[21] Appl. No.: 606,973

[52] U.S. Cl. .......................... 260/533 N; 252/441; 252/456; 252/458; 260/465; 260/3; 260/604 R
[51] Int. Cl.² .................. C07C 51/32; C07C 45/04
[58] Field of Search .................... 260/533 N, 604 R

[56] References Cited

UNITED STATES PATENTS

| 3,642,930 | 2/1972 | Grasselli et al. | 260/533 N X |
| 3,799,979 | 3/1974 | Hensel et al. | 260/533 N |

FOREIGN PATENTS OR APPLICATIONS

| 38,411 | 9/1972 | Japan | 260/533 N |

Primary Examiner—Anton H. Sutto
Attorney, Agent, or Firm—James J. O'Connell

[57] ABSTRACT

A novel catalyst comprising the elements Mo, Bi, Fe, Si, Ni and/or Co and Ru and/or Sb, and, optionally Cl, and an oxidation process, is provided for oxidizing alpha, beta unsaturated monoolefins in the vapor phase with molecular oxygen to produce the corresponding alpha-beta unsaturated carboxylic acid and alpha-beta unsaturated aldehyde. The catalyst can also be used in corresponding ammoxidation reactions.

9 Claims, No Drawings

PROCESS FOR PREPARING UNSATURATED ACIDS AND ALDEHYDES

CROSS REFERENCES TO RELATED PATENT APPLICATIONS

This patent application discloses and claims subject matter which was first disclosed and claimed in U.S. pat. appl. Ser. No. 502,550 filed Sept. 3, 1974, and now abandoned.

BACKGROUND OF THE INVENTION

1. Field of the Invention

The invention relates to the vapor phase catalytic oxidation of alpha,beta-unsaturated monoolefins to the corresponding alpha-beta unsaturated carboxylic acids and alpha-beta unsaturated aldehydes.

2. Description of the Prior Art

The use of oxidation catalysts containing molybdenum and bismuth, alone, or with other selected elements, for the gas phase oxidation of alpha,beta unsaturated monoolefins such as propylene to the corresponding alpha-beta unsaturated acid and/or aldehyde, such as acrylic acid and acrolein, has been known.

In these reactions a gaseous reaction mixture which usually contains the olefin, molecular oxygen and water, as steam, is brought into contact with the catalyst, by continuously passing a stream of the reaction mixture through a bed of the catalyst. Such known catalyst systems would include those disclosed in the following U.S. Pat. Nos. 3,171,859; 3,387,038; 3,445,521; 3,522,299; 3,636,066; 3,642,930; 3,679,603 and 3,691,096.

For commercial purposes this group of catalysts usually comprise the elements Mo, Bi, Fe and Ni and/or Co. In order to improve on the efficiency and/or productivity of such catalyst compositions, and/or the selectivity of the products made with such catalyst compositions it has been desirable, as disclosed in some of the above noted patents, to add additional elements to the catalyst composition.

A review of the prior art and the present applicants' work as illustrated in the examples disclosed below, indicates that the selection of additional elements to be used in combination with the Mo-Bi-Fe-Ni and/or Co based catalyst compositions, to provide the above mentioned improvements, is not an obvious procedure.

The terms % conversion, productivity and % selectivity or efficiency which are employed herein with respect to the present invention are defined as follows (based on the compositions of the gas exiting from the catalyst bed):

I. % conversion = $(A - B/A) \times 100$ where
$A$ = total mol equivalents of olefin fed to the catalyst bed
$B$ = mol equivalents of unconverted olefin in gas exiting from the catalyst bed II. % Efficiency = $(C/A - B) \times 100$ where A and B are as defined above and
$C$ = the mol equivalents of olefin which are present in the alpha,beta unsaturated carboxylic acid and alpha,beta unsaturated aldehyde which are produced.

III. productivity = pounds of alpha-beta unsaturated aldehyde and/or alpha beta unsaturated carboxylic acid produced per cubic foot of catalyst (in the catalyst bed) per hour of reaction time.

SUMMARY OF THE INVENTION

Alpha,beta-unsaturated aliphatic carboxylic acids and alpha,beta unsaturated aliphatic aldehydes are produced with relatively high % conversion, % efficiency and productivity by oxidizing the corresponding alpha,beta-unsaturated aliphatic monoolefin in the vapor phase by contacting the olefin, in the presence of molecular oxygen and steam with certain catalyst compositions containing Mo, Bi, Fe, Si, and Ni and/or Co and Ru and/or Sb, and, optionally, Cl.

An object of the present invention is to provide novel catalyst compositions for the vapor phase oxidation of alpha,beta unsaturated aliphatic monoolefins to the corresponding alpha,beta unsaturated aliphatic carboxylic acid and alpha,beta unsaturated aliphatic aldehyde.

A further object of the present invention is to provide a process whereby alpha,beta unsaturated aliphatic monoolefins can be oxidized in the gas phase so as to produce the corresponding alpha,beta-unsaturated aliphatic carboxylic acid and alpha,beta unsaturated aliphatic aldehyde with a relatively high level of % conversion, % efficiency and productivity.

A further object of the present invention is to provide a process whereby alpha,beta unsaturated monoolefins can be oxidized in the gas phase in the presence of ammonia to produce the corresponding alpha,beta unsaturated nitrile, with a relatively high level of % conversion, % efficiency and productivity.

These and other objects of the present invention are achieved by using as such a catalyst in such processes a composition comprising the elements Mo, Bi, Fe, Si, and Ni and/or Co and Ru and/or Sb, and, optionally, Cl, in the ratio

$$Mo_aBi_bFe_cT_dSi_eX_fCl_g$$

wherein
T is Ni and/or Co,
X is Ru and/or Sb,
$a$ is 10,
$b$ is 0.1 to 5.0, and preferably 0.5 to 1.5,
$c$ is $d/3$ to $d/5$, and preferably $d/3.5$ to $d/5.0$,
$d$ is 2.0 to 9.0, and preferably 4.0 to 8.0,
$e$ is 1 to 20, and preferably 5 to 10,
$f$ is 0.1 to 1.0, and preferably 0.2 to 0.8,
$g$ is 0 to 5, and preferably 1.2 to 5.

The numerical values of $a$, $b$, $c$, $d$, $e$, $f$ and $g$ represent the relative gram-atom ratios of the elements Mo, Bi, Fe, T, Si, X and Cl, respectively, which are initially added to the catalyst composition. After calcination of the composition, as disclosed below, the amounts of the Mo, Bi, Fe, T, Si and X elements remains the same, but only trace amounts, i.e., 0 to about < 0.1 weight percent, of the Cl is still present. The Si which is used in forming the catalyst composition, in the ratios noted above, is other than that which may be present in any support on which the catalyst may be employed, as disclosed below.

THE CATALYST

The elements Mo, Bi, Fe, T, Si and X are present in the catalyst composition in combination with oxygen in the form, it is believed, of various oxides.

The catalyst is preferably prepared from a solution of soluble compounds (salts, complexes or other compounds) of each of the elements Mo, Bi, Fe, T, X, and Si or, in the case of Si, also a colloidal silica sol. The Cl is provided in the form of a soluble salt, and preferably in the form of a chloride of one of the metals Fe, T and X. The solution is preferably an aqueous system having a pH of < 7, and preferably 05. to 3.0, at a temperature of about 20° to 100° C. The solution of the element containing compounds is prepared by dissolving sufficient quantities of soluble compounds of each of the elements, so as to provide the desired $a:b:c:d:e:f:g$ gram-atom ratios of the elements Mo, Bi, Fe, T, Si, X and Cl, respectively. To the extent possible the selected compounds of the various elements should be mutually soluble. The Si compounds are usually added in the form of a colloidal silica sol. Where any of the selected compounds of such elements, other than Si, are not mutually soluble with the other compounds, they can be added last to the solution system. The catalyst composition is then prepared by removing the water or other solvent from the mixture of the compounds in the solution system.

The water or other solvent can be removed by evaporation from the mixture resulting from the combination of all the compounds and solvents.

Where the catalyst is to be used on a support, the compounds of the desired elements are deposited on a porous support usually having a surface area of about 0.1 to 2 square meters per gram. The support has an apparent porosity of 30 to 60%; at least 90% of the pores have a pore diameter in the range of 20–1500 microns. The support is usually used in the form of particles or pellets which are about ⅛to 5/16 inch in diameter. The deposition is accomplished by immersing the support in the ultimate mixture of all the compounds and then evaporating off the major portion of the solvent, and then drying the system at about 80° to 140° C. for 2 to 60 hours. The dried catalyst is then calcined by being heated to 400° to 550° C. for 2 to 24 hours to produce the desired

$Mo_aBi_bFe_cT_dSi_eX_fCl_g$ composition, with the understanding, again, that the Cl content of the calcined support is 0 < 0.1 weight percent. The Cl need only be present during the calcination of the catalyst, it need not be present during the use of the catalyst in the oxidation of the monoolefin to the unsaturated acid and aldehyde.

The supports which may be used include silica aluminum oxide, silicon carbide, zirconia, titania and mixtures thereof.

When used on a support, the supported catalyst usually comprises about 10 to 50 weight % of the catalyst composition, and about 50 to 90 weight % of the support.

The molybdenum is preferably introduced into solution in the form of ammonium salts thereof such as ammonium paramolybdate, and organic acid salts of molybdenum such as acetates, oxalates, mandelates and glycolates. Other water soluble molybdenum compounds which may be used are partially water soluble molybdenum oxides, molybdic acid, and the nitrates and chlorides of molybdenum.

The bismuth, iron, nickel, cobalt, and ruthenium, when used, are preferably introduced into solution in the form of nitrates. Other water soluble compounds of these elements which may be used are the water soluble chlorides and organic acid salts such as the acetates, oxalates, tartrates, lactates, salicylates, formates and carbonates of such elements.

The antimony is preferably introduced into the catalyst system in the form of a water insoluble oxide. A water soluble compound of this element which may be used is antimony trichloride.

When silicon is used it is preferably introduced into the catalyst system in the form of an aqueous colloidal silica ($SiO_2$) sol.

THE MONO-OLEFINS

The alpha,beta unsaturated monoolefins which are oxidized in the process of the present invention are $C_3$ to $C_4$ monoolefins such as propylene, 2-butene and isobutylene. These olefins may be oxidized individually or in combinations thereof.

The principal oxidation products of these olefins in the process of the present invention are as follows:

| Oxidized Olefin | Resulting Carboxylic Acid | Aldehyde |
|---|---|---|
| propylene | acrylic acid | acrolein |
| 2-butene | crotonic acid | crotonaldehyde |
| isobutylene | methacrylic acid | methacrolein |

Where an ammoxidation reaction is conducted the resulting nitrile products are as follows:

| Ammoxidized Olefin | Nitrile |
|---|---|
| propylene | acrylonitrile |
| 2-butene | crotononitrile |
| isobutylene | methacrylonitrile |

THE REACTION MIXTURE

The components of the reaction mixtures which are employed in the oxidation process of the present invention, and the relative ratios of the components in such mixtures, are the following:

1 mole monoolefin,
  0.5 to 3 moles of molecular oxygen (as pure oxygen or in the form of air), and
  0.5 to 20 moles of water (in the form of steam).

The water, or steam, can be used as a reaction diluent and as a heat moderator for the reactions. Other diluents which may be used are inert gases such as nitrogen, CO2 and gaseous saturated hydrocarbons.

The components of the oxidation reaction mixtures are uniformly admixed prior to being introduced into the reaction zone. The components are preheated, individually or after being admixed, prior to their being introduced into the reaction zone, to a temperature of about 200° to 300° C.

In the ammoxidation reaction the reactants include ammonia plus the other reactants noted above.

REACTION CONDITIONS

The preheated oxidation reaction mixture is brought into contact with the catalyst composition, in the reaction zone, under the following conditions:

pressure of about 1 to 10, and preferably of about 2 to 4 atmospheres,
temperature of about 350° to 450° C., and preferably of about 360° to 410° C.,
contact time (reaction mixture on catalyst) of about 0.1 to 10, and preferably of about 0.5 to 3, seconds, and a space velocity of about 1000 to 10,000 h$^{-1}$, preferably 1500 to 5000 h$^{-1}$.

The ammoxidation reaction is conducted under similar conditions.

The contact time may also be defined as the ratio between the apparent volume of the catalyst bed and the volume of the gaseous reaction mixture fed to the catalyst bed under the given reaction conditions in a unit of time.

The reaction pressure in initially provided by the feed of gaseous reactants and diluents, and after the reaction is commenced, the pressure is maintained, preferably, by the use of suitable back-pressure controllers placed on the gaseous effluent side of the catalyst bed.

The reaction temperature is preferably provided by placing the catalyst bed within a tubular converter whose walls are immersed in a suitable heat transfer medium, such as tetralin, molten salt mixtures, or other suitable heat transfer agent, which is heated to the desired reaction temperature.

The following examples are merely illustrative of the present invention and are not intended as a limitation upon the scope thereof.

The examples provided below disclose the preparation of various catalyst compositions, and the use of such compositions in the oxidation of propylene to acrylic acid to acrolein.

The activity of each experimental catalyst was determined in a jacketed 1.049 inch (internal diameter) stainless steel reactor or converter tube 78 inches long equipped with a ⅛inch central thermowell. The jacket contained Dowtherm which served as a heat transfer medium. These experimental reactions were conducted under one of two sets of conditions, i.e., Test Condition A and Test Condition B, which conditions are described below.

TEST CONDITION A

The center portion (about 57–58 inches) of the reactor tube was charged with about 800 ml of catalyst.

The catalysts were tested at about 40 psig with a space velocity of about 4580–4600 hr$^{-1}$ or contact time of about 0.5 seconds, and an inlet feed composed of 3.5 mole % propylene, 9.0 mole % oxygen, 20 mole % steam, and 67.5 mole % nitrogen.

The activity of the catalysts was tested by adjusting the temperature of the reactor tube jacket to produce a maximum temperature (hot spot) of 360+ C. in the catalyst bed, while the oxidation reaction was occurring.

TEST CONDITION B

Test Condition B were the same as that of Test Condition A except as follows:

pressure, psig: 22–24 lbs/in$^2$
volume of catalyst used: 815 ml
space velocity: 3400 hr$^{-1}$
mol % of propylene in inlet feed: 6.2 –6.5
mol % of oxygen in inlet feed: 12.0 –12.5
mol % of H$_2$O (as steam) in inlet feed: 36 –37
mol % of nitrogen in inlet feed: 44–45.8
jacket temperature: 360° C.
hot spot temperatures: 391°–407° C.

Space velocity is calculated by determining the total reactor outlet gas equivalents (liters) of the total effluent evolved over a period of 1 hour. This room temperature volume is converted to the volume of 0° C. at 760 mm Hg.

$$\text{Space Velocity} = \frac{\text{liters of outlet gas equivalents/hour}}{\text{liters of catalyst in reactor}}$$

$$= \frac{1}{\text{hours at 0° C. and atmospheric pressure}}$$

EXAMPLE 2

Catalyst Employed: $Bi_1Mo_{10}Fe_{1.5}Ni_6Sb_{0.5}Si_{10}Cl_{0.6}Ru_{0.2}$

CATALYST PREPARATION

A. Fifty-four grams of bismuth nitrate pentahydrate (0.1122 gram atoms Bi) was dissolved in 39 ml of water containing 6 ml of concentrated nitric acid.

B. Sixty-eight grams of ferric nitrate nonahydrate (0.168 gram atoms Fe) was dissolved in 45 ml water.

C. One-hundred ninety-six grams of nickel nitrate hexahydrate was dissolved in 95 ml of water.

D. Six and twenty-two hundredths grams of hydrated ruthenium trichloride containing 36.5% Ru, (0.0024 gram atoms Ru) was dissolved in 100 ml of water.

E. The bismuth nitrate solution (A) was added to the ferric nitrate solution (B) and then added to the nickel nitrate solution.

F. One-hundred ninety eight grams of ammonium paramolybdate (1.122 gram atoms Mo) was dissolved in 300 ml of water while stirring at 60–80° in a steam-jacketed stainless steel vessel (12⅜inch diameter by 5⅜inch deep evaporating dish). Eight and two-tenths grams of antimony trioxide (Sb$_2$O$_3$) powder (0.0561 grams atoms Sb) was added to the molybdate solution to form a suspension while stirring.

The Bi-Fe-Ni solution (E) and the ruthenium chloride solution (D) was then separately and simultaneously fed to the Mo-Sb mixture (F) over a period of 10 minutes at 50°–60° C., while stirring.

The above slurry was diluted with 400 ml of water and 225 grams of LUDOX "AS" (ammonium stabilized colloidal silica containing 1.122 gram atoms Si) was added while stirring.

Seven-hundred seventy grams (1 liter) of Norton SA-5205, ¼ inch silica-alumina spheres was added to the above slurry and the pH was adjusted to ⅓ at 59° C. with NH$_4$OH and the salts were deposited onto the support by evaporating off the water while stirring manually on a steam bath.

The partially dried impregnated spheres were removed from the evaporator and dried overnight at 115°–120° C., and calcined at 450° C. for 6 hours in the presence of air.

The finished catalyst contained 22.0% including the colloidal silica which amounts to 4.35% of the catalyst. Approximately 66% of the theoretical amount of oxides applied in the form of various salts, adhered to the support. The gram atom ratio of the components of the catalyst prior to calcining, the weight % of oxides in the calcined catalyst, and the calcining temperature are tabulated below in Table I.

When used to oxidize propylene under Test Condition A noted above the catalyst provided conversion, efficiency and productivity results as shown below in Table II.

EXAMPLES 1 AND 3–12

The catalysts for Examples 1 and 3–12 were prepared in a manner analogous to the procedure used in Example 2 with adjustments in the amounts of the elements (other than Bi and Mo) employed to give the gram-atom ratios required, or by deletion of certain elements as required. The gram atom ratios of the components of catalysts 1, 3–12 prior to calcining, the weight % of the oxides in the calcined catalyst, and the calcining temperature used for each catalyst are tabulated below in Table I. Catalysts 1, 3–12 were also evaluated in Test Condition A and the test results are also shown in Table II.

The catalysts of Examples 1, 2, 7, 10 and 12 represent catalyst compositions of the present invention. The catalyst compositions of Examples 3–6, 8–9 and 11 are comparative materials. A comparison of the oxidation test results listed for catalysts 1–12 in Table II shows the advantages, in terms of % conversion, % efficiency and productivity of the catalyst compositions of the present invention, in comparison to the corresponding results obtained with the comparison catalyst systems.

EXAMPLES 13–22

The catalysts for Examples 13–22 were prepared in a manner analogous to the procedure used in Example 1 with adjustments in the amounts of the elements (other than Mo) employed to give the gram-atom ratios required, or by deletion of certain elements as required. The gram-atom ratios of the components of catalysts 13–22 prior to calcining, the weight % of the oxides in the calcined catalyst, and the calcining temperature used for each catalyst are tabulated below in Table III. Catalysts 13–22 were also evaluated in Test Condition B and the test results are shown below in Table IV.

TABLE I

COMPOSITION AND CALCINING TEMPERATURE OF CATALYSTS OF EXAMPLES 1–12

| Example | Gram-Atom Ratio of Catalyst prior to calcination | Weight % of Oxides in Catalyst* | 6 Hour Calcining Temperature, °C. |
|---|---|---|---|
| 1 | $Mo_{10}Bi_1Fe_{1.3}Ni_6Si_{10}Ru_{0.5}Cl_{0.5}$ | 21.2 | 450 |
| 2 | $Mo_{10}Bi_1Fe_{1.3}Ni_6Si_{10}Ru_{0.5}Sb_{0.3}Cl_{0.6}$ | 22.0 | 450 |
| 3 | $Mo_{10}Bi_1Fe_{1.14}Ni_4Si_5$ | 21.4 | 470 |
| 4 | $Mo_{10}Bi_1Fe_{1.33}Ni_4Si_{10}$ | 23.5 | 450 |
| 5 | $Mo_{10}Bi_1Fe_{1.38}Ni_{3.5}Si_7$ | 23.2 | 490 |
| 6 | $Mo_{10}Bi_1Fe_{1.75}Ni_7Si_{10}$ | 27.0 | 488 |
| 7 | $Mo_{10}Bi_1Fe_{1.3}Ni_6Si_{10}Sb_{0.5}$ | 22.3 | 450 |
| 8 | $Mo_{10}Bi_1Fe_{0.96}Ni_{4.75}Sb_{0.33}$ | 20.5 | 490 |
| 9 | $Mo_{10}Bi_1Fe_{1.75}Ni_7Sb_{0.5}$ | 17.1 | 470 |
| 10 | $Mo_{10}Bi_1Fe_{1.3}Ni_{6.5}Si_7Sb_{0.25}$ | 22.8 | 490 |
| 11 | $Mo_{10}Bi_1Fe_{1.75}Ni_7Si_{10}Cl_5$ | 25.8 | 477 |
| 12 | $Mo_{10}Bi_1Fe_{1.3}Ni_{6.5}Si_7Sb_{0.25}Cl_{1.2}$ | 26.6 | 490 |

*After calcination, and assuming that the Cl content is zero.

TABLE II

OXIDATION TEST RESULTS FOR CATALYSTS OF EXAMPLES 1–12

| | | | Productivity, lb/ft³cat/hour | | |
|---|---|---|---|---|---|
| Example | % Conversion | % Efficiency | Acrolein | Acrylic Acid | Total Acrolein + Acrylic Acid |
| 1 | 74.2 | 89.2 | 14.49 | 1.60 | 16.09 |
| 2 | 78.8 | 89.8 | 15.16 | 1.93 | 17.09 |
| 3 | 52.3 | 89.5 | 10.04 | 0.62 | 10.66 |
| 4 | 53.1 | 87.1 | 9.61 | 0.65 | 10.26 |
| 5 | 60.0 | 88.6 | 10.92 | 0.82 | 11.74 |
| 6 | 65.5 | 85.7 | 12.44 | 0.89 | 13.33 |
| 7 | 74.1 | 87.1 | 14.17 | 1.39 | 15.56 |
| 8 | 46.8 | 92.7 | 9.78 | 0.42 | 10.20 |
| 9 | 42.2 | 87.8 | 8.08 | 0.27 | 8.35 |
| 10 | 66.9 | 89.3 | 13.35 | 0.97 | 14.32 |
| 11 | 67.6 | 86.9 | 13.02 | 0.64 | 13.66 |
| 12 | 70.9 | 91.4 | 14.75 | 0.98 | 15.73 |

TABLE III

COMPOSITION AND CALCINING TEMPERATURE OF CATALYSTS OF EXAMPLES 13–22

| Example | Gram-Atom Ratio of Catalyst prior to Calcination | Weight % of Oxides in Catalyst* | 6 Hour Calcining Temperature, °C. |
|---|---|---|---|
| 13 | $Mo_{10}Bi_1Fe_{1.38}Ni_{3.5}Si_7$ | 23.2 | 490 |
| 14 | $Mo_{10}Bi_1Fe_{2.3}Ni_7Si_1$ | 19.0 | 500 |
| 15 | $Mo_{10}Bi_1Fe_{1.33}Ni_6Si_{10}Sb_{0.25}$ | 28.5 | 490 |
| 16 | $Mo_{10}Bi_1Fe_{1.22}Ni_{6.5}Si_{10}Sb_{0.33}Cl_{1.2}$ | 27.9 | 490 |
| 17 | $Mo_{10}Bi_1Fe_{1.18}Ni_{6.5}Si_{10}Sb_{0.25}Cl_{2.4}$ | 28.4 | 490 |
| 18 | $Mo_{10}Bi_{0.91}Fe_{1.14}Ni_{5.91}Si_{9.1}Sb_{0.23}Cl_{1.09}$ | 28.8 | 491 |
| 19 | $Mo_{10}Bi_{1.11}Fe_{1.07}Ni_{7.22}Si_{11.1}Sb_{0.28}Cl_{1.33}$ | 26.2 | 490 |
| 20 | $Mo_{10}Bi_{1.25}Fe_{1.66}Ni_{8.1}Si_{12.5}Sb_{0.31}Cl_{1.60}$ | 27.1 | 490 |

TABLE III-continued

COMPOSITION AND CALCINING TEMPERATURE OF CATALYSTS OF EXAMPLES 13-22

| Example | Gram-Atom Ratio of Catalyst prior to Calcination | Weight % of Oxides in Catalyst* | 6 Hour Calcining Temperature, °C. |
|---|---|---|---|
| 21 | $Mo_{10}Bi_1Fe_{1.1}Ni_{8.5}Si_{10}Sb_{0.25}Cl_{2.0}$ | 27.2 | 490 |
| 22 | $Mo_{10}Bi_1Fe_{1.3}Ni_{8.5}Si_7Sb_{0.25}Cl_{1.2}$ | 35.4 | 485 |

*after calcination, and assuming that the Cl content is zero.

TABLE IV

OXIDATION TEST RESULT FOR CATALYSTS OF EXAMPLES 13-22

| | | | Productivity, lbs/ft³cat./hour | | |
|---|---|---|---|---|---|
| Example | % Conversion | % Efficiency | Acrolein | Acrylic Acid | Total acrolein + Acrylic Acid |
| 13 | 50.5 | 90.5 | 14.01 | 1.36 | 15.37 |
| 14 | 53.2 | 66.1 | 11.09 | 0.67 | 11.76 |
| 15 | 66.0 | 87.5 | 16.83 | 1.97 | 18.80 |
| 16 | 69.3 | 91.5 | 18.36 | 2.31 | 20.67 |
| 17 | 64.1 | 92.1 | 17.39 | 1.72 | 19.11 |
| 18 | 71.4 | 91.8 | 17.67 | 2.64 | 20.31 |
| 19 | 77.5 | 84.5 | 18.86 | 2.62 | 21.48 |
| 20 | 72.7 | 84.8 | 17.03 | 2.45 | 19.48 |
| 21 | 55.8 | 92.5 | 16.64 | 1.00 | 17.64 |
| 22 | 71.2 | 88.2 | 18.83 | 1.72 | 20.55 |

The catalysts of Examples 15 to 22 represent catalyst compositions of the present invention. The catalyst compositions of examples 13 and 14 are comparative materials. A comparison of the oxidation test results listed for catalysts 13-22 in Table IV shows the advantages in terms of % conversion, % efficiency and productivity of the catalyst compositions of the present invention, in comparison to the corresponding results obtained with the comparison catalyst systems.

For the purposes of further definition, the following terms employed in the catalyst evaluation are given (basis of calculation = outlet gas composition):

% Conversion =

$$\frac{(\text{Total } C_3H_6 \text{ Equivalents}) - (\text{Unconverted } C_3H_6)}{(\text{Total } C_3H_6 \text{ Equivalents})} \times 100$$

% Efficiency =

$$\frac{(C_3H_6 \text{ Equivalents of Acrolein and Acrylic Acid})}{(\text{Total } C_3H_6 \text{ Equivalents}) - (\text{Unconverted } C_3H_6)} \times 100$$

Productivity =

$$\frac{(\text{Gms of Component/Hr}) 28.32}{(453.6)(\text{Catalyst Volume Tube, Liters})} = \text{Lbs/Hr-Ft}^3 \text{ Catalyst}$$

What is claimed is

1. A process for the production of $C_3$ to $C_4$ alpha-beta unsaturated aliphatic carboxylic acid and $C_3$ to $C_4$ alpha-beta unsaturated aliphatic aldehyde by vapor phase catalytic oxidation of the corresponding unsaturated $C_3$ to $C_4$ mono-alpha-olefin with molecular oxygen in the presence of steam which comprises contacting the reaction mixture with a calcined oxidation catalyst which is devoid of potassium and which contains the elements Mo, Bi, Fe, T, Si and X in the form of oxides and which contains the elements Mo, Bi, Fe, T, Si, X and Cl, prior to calcination, in the ratio

wherein
T is selected from the group consisting of Ni and Co,
X is selected from the group consisting of Ru and Sb,
$a$ is 10,
$b$ is 0.1 to 5.0,
$c$ is $d/3$ to $d/5$,
$d$ is 2.0 to 9.0,
$e$ is 1 to 20,
$f$ is 0.1 to 1.0, and
$g$ is 0 to 5.

2. A process as in claim 1 in which propylene is oxidized to produce acrolein and acrylic acid.

3. A process as in claim 2 in which said oxidation catalyst is supported on an inert support.

4. A process as in claim 3 in which said support is silica, alumina or silica-alumina.

5. A process as in claim 3 in which $b$ is 0.5 to 1.5, $C$ is $d/3.5$ to $d/5$, $d$ is 4.0 to 8.0, $e$ is 5 to 10, $f$ is 0.2 to 0.8 and $g$ is 1.2 to 5.

6. A process as in claim 1 in which T comprises Ni.

7. A process as in claim 6 in which X comprises Ru.

8. A process as in claim 6 in which X comprises Sb.

9. A process as in claim 8 in which X consists of Ru and Sb.

* * * * *